United States Patent [19]

Borgersen, deceased et al.

[11] 4,361,034

[45] Nov. 30, 1982

[54] PORTABLE HARDNESS TESTER

[75] Inventors: Roland D. Borgersen, deceased, late of Bryn Mawr, Pa., by Lula A. Borgersen, administrator; James G. Mullen, Bala Cynwyd, Pa.; James W. Lineberger, Wenonah, N.J.

[73] Assignee: King Tester Corporation, King of Prussia, Pa.

[21] Appl. No.: 234,393

[22] Filed: Feb. 13, 1981

[51] Int. Cl.³ .............................................. G01N 3/42
[52] U.S. Cl. ...................................................... 73/81
[58] Field of Search ............................... 73/81, 82, 83

[56] References Cited

U.S. PATENT DOCUMENTS

| | | | |
|---|---|---|---|
| 1,209,350 | 12/1916 | Steiner . | |
| 1,232,782 | 7/1917 | Field | 73/81 |
| 1,384,389 | 7/1921 | Johnson | 73/81 |
| 1,770,045 | 7/1930 | Shore et al. . | |
| 1,973,333 | 9/1934 | Craemer | 265/19 |
| 2,448,486 | 8/1948 | Chester | 73/81 |
| 2,466,567 | 4/1949 | Williams | 73/81 |
| 2,643,544 | 6/1953 | Chester | 73/81 |
| 2,693,698 | 11/1954 | Scott | 73/83 |
| 2,835,127 | 5/1958 | Scott | 73/81 |
| 2,976,723 | 3/1961 | Eddy | 73/94 |
| 3,128,621 | 4/1964 | Scott | 73/81 |
| 3,129,582 | 4/1964 | Borgersen | 73/81 |
| 3,138,951 | 6/1964 | Scott . | |
| 3,486,373 | 12/1969 | Scott | 73/141 |
| 3,754,436 | 8/1973 | Saxton | 73/81 |
| 4,036,048 | 7/1977 | Webster | 73/81 |
| 4,094,188 | 6/1978 | Bellouin et al. | 73/81 |
| 4,147,052 | 4/1979 | Tsujiuchi et al. | 73/81 |

FOREIGN PATENT DOCUMENTS 2357755  6/1974  Fed. Rep. of Germany .
2751095  3/1979  Fed. Rep. of Germany .

OTHER PUBLICATIONS

Introdyne Universal Horizontal Hardness Tester, (Blue River Laboratories, R.D. #4, Box 76, Lewistown, Pennsylvania 17044).

Hirth Minimeter for Accurate Measuring, (Falkimer Machinery Co. Pty, Ltd., Famacoy House, Goulburn Street, Sydney, Australia).

Primary Examiner—S. Clement Swisher
Attorney, Agent, or Firm—Austin R. Miller

[57] ABSTRACT

Apparatus for supporting a metal hardness test head comprises a base with a plurality of coplanar petal-like supports integral with and extending outwardly from a lower part thereof, an elevating screw in threaded engagement with said base and including a lateral bore therein communicating with a lateral bore of the base, means within the communicating lateral bores for bracing the elevating screw against movement relative to the base and a carriage for supporting a test head above the base, movable along the elevating screw.

13 Claims, 9 Drawing Figures

PORTABLE HARDNESS TESTER

BACKGROUND OF THE INVENTION

1. Field of the Invention

This invention relates to portable support apparatus for test heads used to test material hardness according to the Brinell method.

2. Description of the Prior Art

The portable hardness tester disclosed and claimed in U.S. Pat. No. 3,129,582 has been generally highly successful. However, problems do exist with the '582 apparatus, including relatively poor stability of the base supporting the test head, inability to replace elevating screws along which the test head support carriage travels, susceptibility to failure of the bearing carrying a rotatable shaft used for raising and lowering the carriage (with consequent jamming of the gear assembly which raises and lowers the carriage) and loosening of the spindle associated with a rear elevating screw resulting in rough operation during raising and lowering of the carriage and causing jamming of the gear train.

SUMMARY OF THE INVENTION

This invention provides highly portable apparatus adapted for supporting a Brinell method metal hardness test head.

The apparatus may include a base having a central portion of generally rectangular parallelepiped configuration; a plurality of coplanar petal-like supports integral with and extending outwardly from a lower part of the central portion, where downwardly facing surfaces of the central portion and the supports are coplanar and contiguous with one another. The base may further include an anvil support portion integral with and extending laterally in cantilever fashion from the base central portion at a position remote from the downwardly facing surface of the central portion. The anvil support portion has an upwardly facing planar anvil support surface. An anvil may rest on the anvil support surface. The base further includes webs generally perpendicular to the contiguous downwardly facing surfaces of the petal-like supports, integral with the base central portion, providing bracing between upper surfaces of the petal-like supports and lateral surfaces of the base central portion. The base central portion includes a threaded bore perpendicular to and opening oppositely from the downwardly facing contiguous surfaces with the base central portion also including at least one external lateral bore perpendicular to and intersecting with the threaded bore.

The apparatus may further include an elevating screw in threaded engagement with the threaded bore and having a lateral bore communicating with the lateral bore in the base central portion.

Means within the communicating lateral bores brace the elevating screw against movement relative to the base.

A carriage may be provided supporting the test head above the anvil and may be movable along the elevating screw. The carriage may include a pair of spaced-apart parallel side plates bracketing the elevating screw therebetween, a spacer block between and connecting the side plates with the elevating screw passing through the spacer block, a spindle journaled in the spacer block for rotation about an axis parallel with the elevating screw where the spindle drivingly engages the threaded elevating screw, an idler gear journaled between the parallel plates of the carriage for rotation about an axis to drivingly engage external teeth of the spindle, a driven bevel gear on a common shaft and rotatable unitarily with the idler gear, a driving bevel gear mounted on and rotatable unitarily with a shaft drivingly engaged by the driven bevel gear, where the shaft extends through a first side plate and has a cranking handle fixedly connected to the shaft outboard of the first side plate for facilitating rotation of the shaft by an operator turning the handle.

A bearing collar may be provided separating the driving bevel gear and shaft from the first side plate. The bearing collar is preferably immovable with respect to the first side plate, includes a shoulder portion having axial length at least equal to thickness of the first side plate and has an axial bore therethrough receiving the shaft. The bearing collar further includes a flange portion contacting the inwardly facing surface of said first side plate and extending radially outwardly about the shoulder portion at least to a point where the bevel gear periphery is at least oblique to the inwardly facing surface of the first plate.

BRIEF DESCRIPTION OF THE DRAWINGS

FIG. 6 is a sectional view taken at 6—6 in FIG. 1.

FIG. 9 is an isometric view of a fastener embodying a portion of the invention.

DESCRIPTION OF THE PREFERRED EMBODIMENTS

Figure 1:
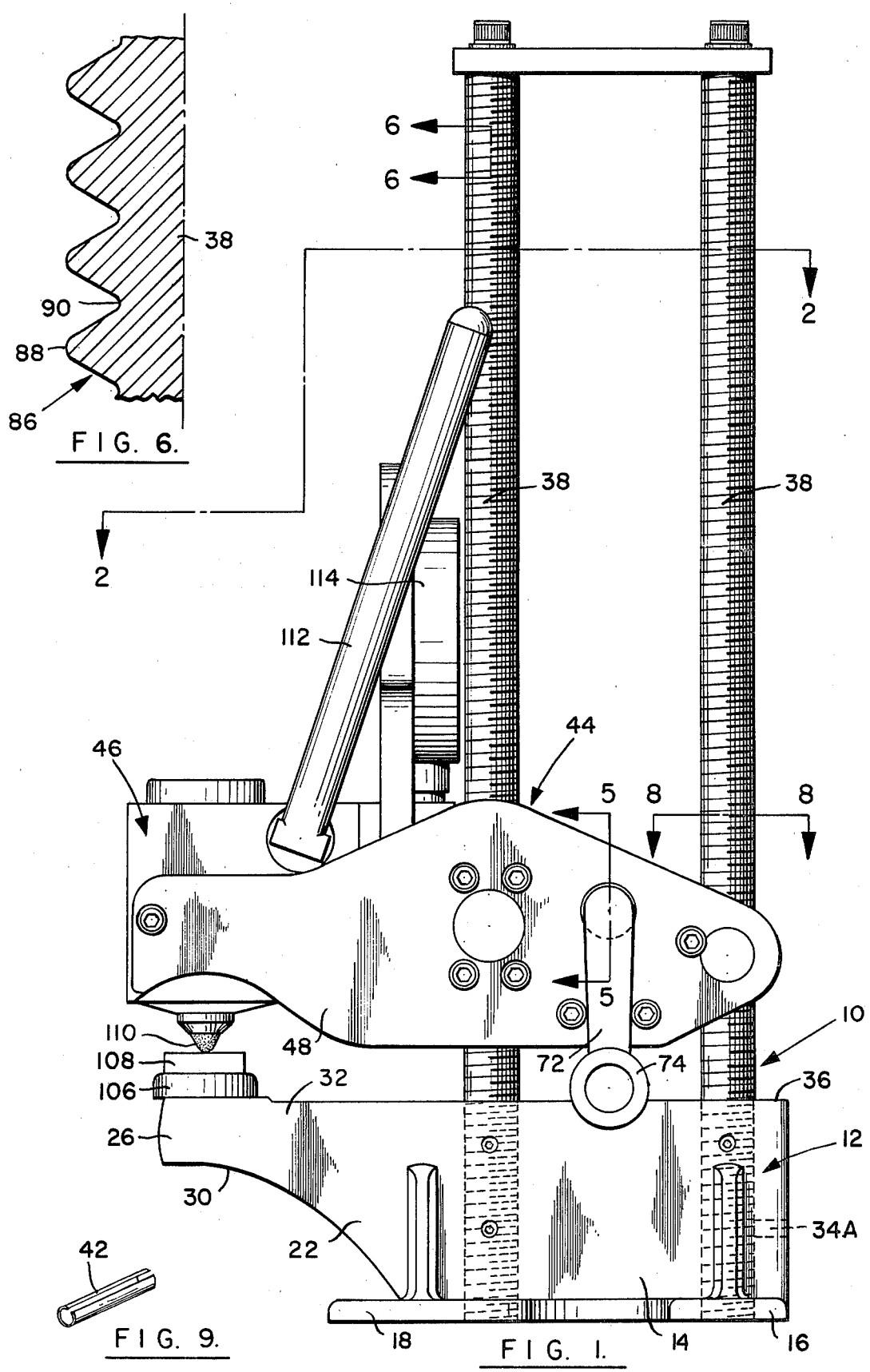
FIG. 1 is a side view of portable support apparatus for a metal hardness test head, showing the test head in place.
Figure 2:
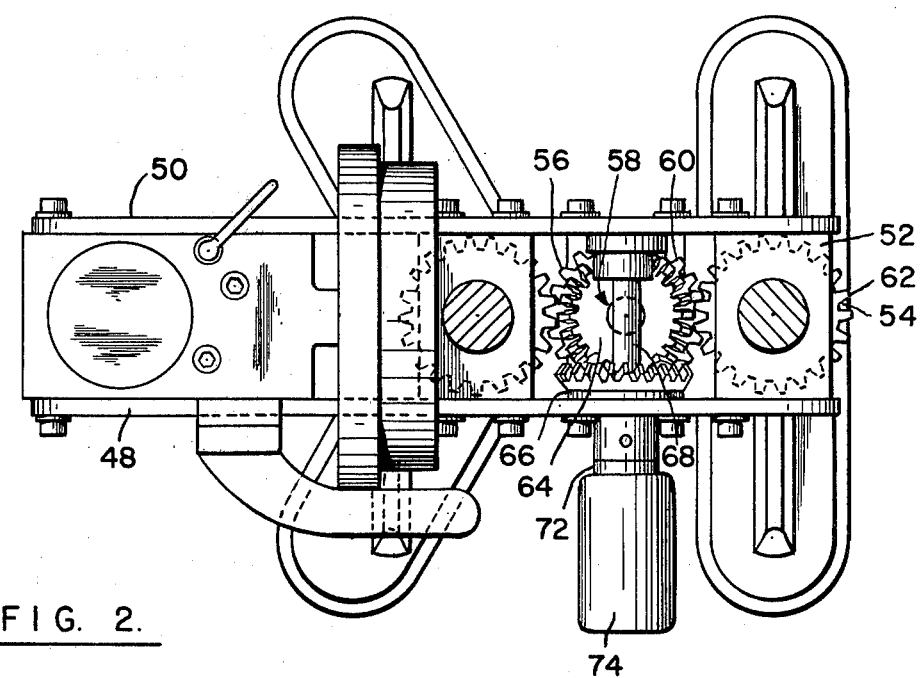
FIG. 2 is a sectional view taken at 2—2 in FIG. 1.
Figure 3:
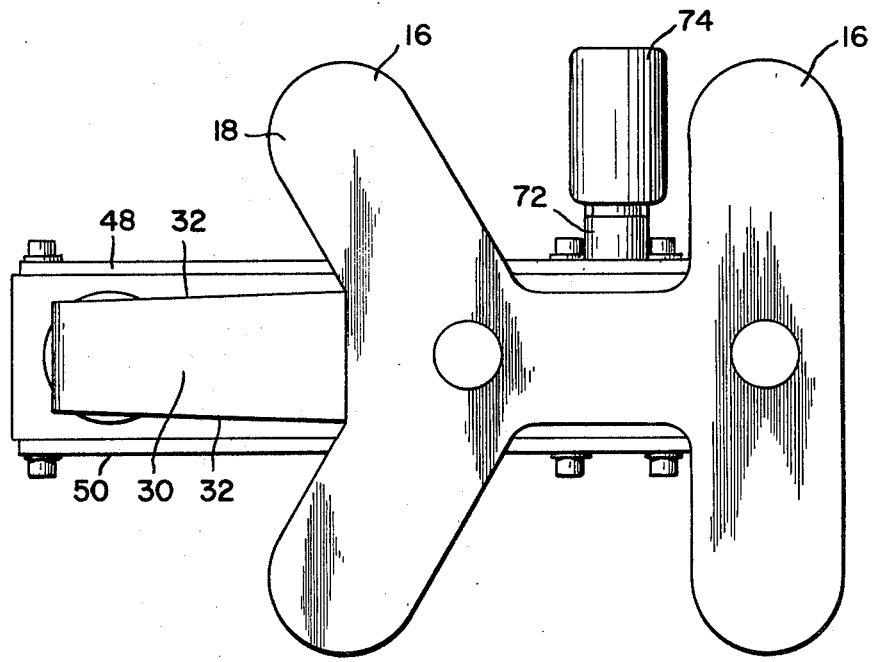
FIG. 3 is a bottom view of apparatus depicted in FIGS. 1 and 2.
Figure 4:
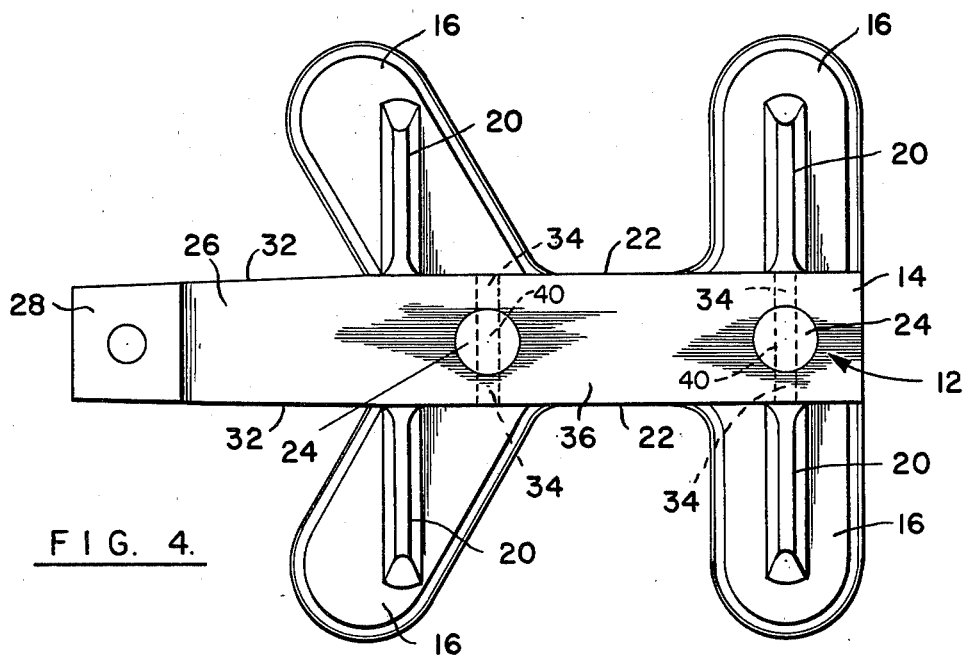
FIG. 4 is a top view of the base portion of support apparatus depicted in FIG. 1.

Apparatus for supporting a metal hardness test head, preferably a Brinell method metal hardness test head, is illustrated in side elevation in FIG. 1 and is denoted generally 10. Apparatus 10 includes a base, designated generally 12, which includes a central portion 14 of generally rectangular parallelepiped configuration and a plurality of petal-like supports 16 integral with and extending outwardly from a lower part of base central portion 14. Petal-like supports 16 are preferably all co-planar one with another and formed integrally with central portion 14 of base 12. Downwardly facing surfaces of central portion 14 and supports 16 are all preferably co-planar and contiguous with one another to present a broad, single, flat lower surface of support apparatus 10, as shown in FIG. 3. As seen in FIGS. 2, 3 and 4, petal-like supports 16 extend laterally quite far from central portion 14, providing high stability for the test head support apparatus 10. The continuous flat downwardly facing surface 18 of base central portion 14 and supports 16 provides a broad lower support surface for support apparatus 10, with lateral extremities of support surface 18 removed from base central portion 14 a distance greater than width of base central portion 14. This provides a low center of gravity for the support apparatus, contributing to high stability and resistance to tipping.

A plurality of generally vertical webs 20 are provided with each web 20 providing bracing between an upper surface of a petal-like support 16 and a lateral surface 22 of base central portion 14. Webs 20 are formed integrally with central portion 14 and supports 16 and thereby contribute to the low center of gravity characteristic of the base 12 and therefore of the support apparatus 10.

Base central portion 14 includes threaded bores 24 formed generally perpendicular to and opening at least upwardly, oppositely from downwardly facing contiguous support surface 18. Bores 24 may also extend entirely through base central portion 14 and exit therefrom at surface 18, as illustrated.

Base 12 has an anvil support portion 26 formed integrally with and extending laterally in cantilever fashion from central portion 14. Anvil support portion 26 is formed remote from downwardly facing surface 18 and includes an upwardly facing planar anvil support surface 28 which is preferably parallel with lower surface 18. A lower surface 30 of anvil support portion 26 tapers upwardly and away from the downwardly facing surface 18 of central portion 14 as shown in FIG. 1. While downwardly facing surface 30 has been illustrated as an arcuate surface in FIG. 1, arcuate configuration is not necessary.

Similarly to lower surface 30, lateral surfaces 32 of anvil support portion 26 taper inwardly away from lateral surfaces 22 of central portion 14 of base 12 to define, with downwardly facing surface 30, anvil support portion 26 having substantially reduced width and height, relative to central portion 14, at the extremity of anvil support portion 26 laterally most remote from central portion 14. The reduced width and height of anvil support portion 26 relative to central portion 14 is illustrated in FIGS. 1, 3 and 4.

Base 12 including central portion 14, petal-like supports 16, webs 20 and anvil support portion 26 is preferably formed as a unitary piece of cast aluminum with central portion 14, supports 16, webs 20 and anvil support portion 26 all being integral one with another.

Base 12 preferably includes lateral bores 34 perpendicular to and intersecting with threaded bores 24, where lateral bores 34 communicate with both exterior lateral surfaces of base 12 and with threaded bores 24. Preferably threaded bores 24 extend entirely through base 12, exiting centrally of lower surface 18 and of upper surface 36 of base 12; this is best seen in FIGS. 1 and 4.

An elevating screw 38 is received by and is preferably in threaded engagement with each threaded bore 24 of base 12. Two elevating screws may be utilized as illustrated in FIGS. 1 and 2. Elevating screw 38 is preferably in threaded engagement with its threaded bore 24 over the entire length thereof as shown in FIG. 1. Each elevating screw 38 includes a lateral bore 40 therein communicating with an external lateral bore 34 in base 12. Lateral bores 40 may be formed in screws 38 by drilling thereinto via lateral bores 34 after screws 38 have been threaded into bores 24. In this manner, communication between bores 40 and 34 is assured.

Residing within at least a portion of one of bores 40 and a lateral bore 34 is means for bracing elevating screw 38 against movement relative to base 12; this means is preferably a hollow longitudinally slotted cylindrical member made of highly elastic spring steel. The slotted cylindrical member is illustrated in FIG. 9 and may be force fitted into communicating lateral bores 34 and 40. During the force fit procedure cylindrical member 42 is urged to a smaller diameter by closing the longitudinal gap therein by hand. Once member 42 is inserted to where member 42 resides within lateral bores 34, 40, the spring-like character of member 42 urges the curved exterior surface thereof against the cylindrical internal surfaces of communicating lateral bores 34, 40; this resilient spring-like action secures hollow cylindrical member 42 tightly in place. Since member 42 has a portion thereof resident in lateral bore 34 and a portion thereof resident in lateral bore 40 and is highly resistant to deflection transverse to the longitudinal axis, member 42 effectively prevents relative movement of elevating screw 38 with respect to base 12.

Figure 8:
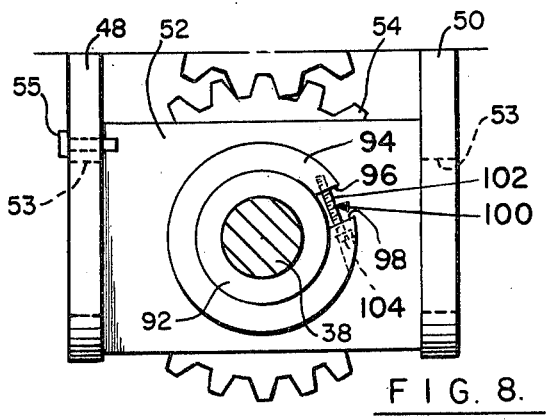
FIG. 8 is a broken sectional view taken at 8—8 in FIG. 1, illustrating an optional embodiment of the invention.

A carriage designated generally 44 supports the test head, designated generally 46, above anvil support surface 28 of anvil support portion 26 and is movable vertically along elevating screws 38. Carriage 44 includes a pair of spaced-apart parallel side plates 48, 50 with spacing of plates 48, 50 permitting elevating screws 38 to be bracketed therebetween as shown in FIG. 2. A spacer block 52 is between and connected to respective side plates 48, 50 and includes a vertical passageway receiving an elevating screw 38 therewithin. Spacer block 52 includes rounded shoulders 53 projecting laterally therefrom as shown in FIG. 8. Shoulders 53 are complementally received by unnumbered bores of corresponding size in side plates 48, 50 and, in combination with the unnumbered bores, accurately position block 52 with respect to the side plates. Block 52 is secured to side plates 48, 50 by machine screws 55 passing through respective side plates 48, 50 and threadedly engaging unnumbered threaded bores in spacer block 52; to aid clarity of FIG. 8 only one (1) screw 55 is illustrated. Likewise, two spacer blocks 52 are provided, one associated with each elevating screw 38.

Journaled within the vertical passageway through each spacer block 52 is an internally and externally toothed spindle 54, journaled for rotation with respect to spacer block 52 about an axis parallel to the passageway through spacer block 52. Internal teeth of each spindle 54 drivingly engage the respective threaded elevating screw 38. Rotation of spindles 54 about elevating screws 38 raises and lowers carriage 44 along the elevating screws. Internal teeth of spindles 54 have not been illustrated in FIG. 2, where a spindle 54 is shown, to aid the clarity of the drawing.

An idler gear 56 is journaled between plates 48, 50 for rotation on a vertical shaft 58; teeth 60 of idler gear 56 drivingly engage external teeth 62 of spindles 54. Idler gear 56 is only partially visible in FIG. 2, being hidden behind driven bevel gear 64 which is mounted on first shaft 58 commonly with idler gear 56. Part of idler gear 56 is also visible in FIG. 8. The accurate positioning of spacer block 52 along side plates 48, 50 resulting from complemental receipt of rounded shoulders 53 by the unnumbered bores, as discussed above, provides proper spacing of spindle 54 with respect to idler gear 56 for optional engagement of idler gear 56 with external teeth 62 of spindle 54.

A driving bevel gear 66 is mounted on and rotates unitarily with a second shaft 68; bevel gear 66 drivingly engages driven bevel gear 64. Second shaft 68 extends through first side plate 48 and is journaled within a bearing collar designated generally 70, shown in FIG. 5.

A cranking handle 72 is secured to and rotatable unitarily with second shaft 68 and is located outboard of first side plate 48. Cranking handle 72 facilitates rotation of second shaft 68 upon an operator turning a knob portion 74 rotatably associated with cranking handle 72.

Bearing collar 70 separates driving bevel gear 66 and second shaft 68 from first side plate 48 and is immovable with respect to first side plate 48. Bearing collar 70 includes a shoulder portion 76 having axial length at least equal to the thickness of side plate 48. An axial bore of bearing collar 70 has a tubular shoulder extension portion of driving bevel gear 66 journaled therein for rotation of second shaft 68 relative to bearing collar 70.

Figure 5:
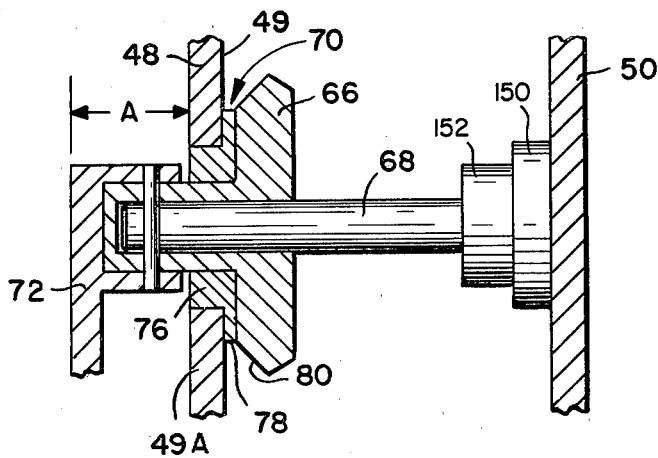
FIG. 5 is a sectional view taken at 5—5 in FIG. 1.

Bearing collar 70 also includes a flange 78 which abuts an inwardly facing surface of first plate 48. Flange 78 extends radially outwardly about shoulder 76 of bearing collar 70 at least to where the periphery of driving bevel gear 66 is no longer parallel to and is at least oblique to inwardly facing surface 49 of first plate 48. The surface of driving bevel gear 66 which is oblique relative to inwardly facing surface 49 of first plate 48 is denoted 80 in FIG. 5. Such radial extension of flange 78 assures that driving bevel gear 66 does not contact side plate 48. The end of second shaft 68 opposite bearing collar 70 may be journaled for rotation with respect to second side plate 50 in any suitable manner. Specifically, a journal denoted 150 in FIG. 5 may receive an end of shaft 68 and be secured to side plate 50. An adjustable collar 152 in FIG. 5 may be secured about shaft 68 by a setscrew so that adjustable collar 152 turns unitarily with shaft 68 and is in running contact with journal 150 during shaft rotation. When collar 152 is positioned as depicted in FIG. 5 and the setscrew is tightened so collar 152 and shaft 68 turn unitarily, collar 152 acts to retain driving bevel gear 66 in running contact with the facing surface of bearing collar 70, preventing movement of bevel gear 66 towards side plate 50 and similarly preventing movement of bearing collar 70 out of side plate 48 towards side plate 50. This prevents carriage drive mechanism jamming which otherwise might occur if driving bevel gear 66 contacted driven bevel gear 64 too closely.

Figure 7:
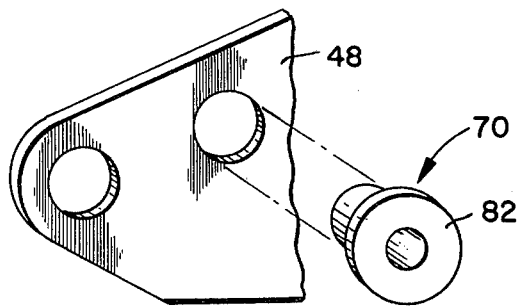
FIG. 7 is a broken perspective view showing structure appearing at the left hand side of FIG. 5.

Bearing collar 70 is preferably pressfitted into first plate 48 with shoulder 76 extending through an aperture therein to a position where an outwardly facing annular surface of shoulder portion 76 is at least flush with outwardly facing surface 49A of first plate 48. Assembly of bearing collar 70 into first side plate 48 is depicted in FIG. 7; bearing collar 70 fully pressfitted into side plate 48 is illustrated in FIG. 5. Bearing collar 70 is preferably brass with shoulder and flange portions 76, 78 formed integrally one with another. Flange 78 of bearing collar 70 abuts inwardly facing surface 49 of first side plate 48 and presents an outwardly facing annular surface 82 axially remote from the shoulder 76; surface 82 is in running contact with driving bevel gear 66 during rotation of second shaft 68 due to rotation of cranking handle 72. Similarly the outwardly facing annular surface presented by shoulder 76 remote from flange 78 is in running contact with cranking handle 72 and separates cranking handle 72 from surface 49A of first side plate 48.

Threads 86 of elevating screws 38 have curved crests 88 and roots 90 as shown in FIG. 6. The complementally mating internal teeth of spindles 54 have complementally curved crests and roots for close fitting threaded engagement with crests 88 and root 90 of threads 86 of elevating screws 38.

Referring to FIG. 8, each spindle 54, journaled within spacer block 52 for rotation with respect thereto, is in threaded engagement with an elevating screw 38. In this embodiment spindle 54 includes an annular sleeve protruding outwardly from within spacer block 52, with the annular sleeve slideably receiving elevating screw 38 therewithin; the sleeve is denoted 92 in FIG. 8.

Securing spindle 54 against downward movement relative to spacer block 52 is an annular ring 94 coaxial with and secured about sleeve 92 externally of spacer block 52. Ring 94 has a radial cut therethrough providing a gap between ring ends 96, 98 defined by the cut. A setscrew 100 bridges the gap between ends 96, 98 and urges ring 94 closed at the gap upon setscrew rotation. A shaft portion 102 threadedly engages a tapped hole in ring 94. The head portion 104 of setscrew 100 interferes with the portion of ring 94 across the gap from the tapped hole, resulting in closure of the gap between ends 96, 98 upon setscrew rotation.

The setscrew axis is preferably generally tangential to ring 94. Ring 94 interferes with spacer block 52 upon movement of spindle 54 along elevating screw 38 in a direction away from ring 94, thereby requiring spacer block 52 and hence carriage 44 to move axially with spindle 54 as spindle 54 rotates about elevating screw 38.

During apparatus operation an anvil portion 106 may be provided, above anvil support portion 26, resting on anvil support surface 28. A workpiece 108 is placed on anvil 106 and carriage 44 lowered by rotation of cranking handle 72 until contact ball 110 of test head 46 contacts workpiece 108. The operator then operates handle 112 to move contact ball 110 downwardly with a selected force. The operator reads the selected force from meter 114. After the selected force is applied to the workpiece, the workpiece is removed and diameter of the depression produced by contact ball 110 is measured; measured diameter of the arcuate depression in the workpiece is then correlated to Brinell hardness. Details of the test head are disclosed in U.S. Pat. No. 3,129,582.

The large area of lower surface 18 of base 12 combined with the substantial mass of the preferably solid aluminum base provides good stability for the test head support apparatus.

The shape of the anvil support portion produced by taper of downwardly facing surface 30 and lateral surfaces 32 allows, in one embodiment, testing of round rings having inner diameter as small as two inches. The rings fit over anvil support portion 26. The narrow nose-like configuration of anvil support portion 26 facilitates testing of workpieces with narrow openings or small holes.

Forming base 12 of cast aluminum facilitates machining to produce flat lower surface 18. Once lower surface 18 is machined flat, surface 18 provides a reference from which to machine the remainder of base 12. Typically anvil support surface 28 is subsequently machined and, with the reference provided by lower surface 18, anvil support surface 28 can be machined parallel to lower surface 18. The reference provided by lower surface 18 also allows bores for threaded elevating screws 38 to be drilled perpendicularly to lower surface 18 and parallel one to another. Threaded engagement of elevating screws 38 in threaded bores 24 facilitates removal of elevating screws 38 in case the elevating screws are damaged through misuse or become worn.

Once bores 24 have been drilled and tapped in base 12, elevating screws 38 are threaded in place to predetermined depth in bores 24. Preferably elevating screws 38 are in threaded engagement with bores 24 over the entire bore length so the elevating screw lower axial extremities are flush with lower surface 18. Lateral bores 34 are drilled in base 12 with drilling continuing to form lateral bores 40 within elevating screw 38. An additional lateral bore is provided as 34A, through the end of base 12 into the more rearward elevating screw 38; see FIG. 1. Hollow cylindrical members 42 are then introduced into and driven through lateral bores 34 until cylindrical members 42 are at least partially received by bores 40. Lateral bore 34A is tapped to receive a setscrew which, in combination with members 42, secures rearward elevating screw 38 in place. The combination of lateral bore 34A and a setscrew is used because webs 20, shown as the more right-hand pair of webs in FIG. 1, prevent drilling a second, lower lateral bore through base 12, from lateral side 22 thereof, into rearward elevating screw 38.

Use of threads 86 having curved roots 90 and crests 88 in elevating screws 38 reduces friction between the internal teeth of spindle 54 and the elevating screws. This makes operation faster and smoother and reduces the chance for jamming of the spindle internal teeth with the elevating screw threads.

The curved roots 90 and crests 88 provide economic advantage. Elevating screws with curved roots and crests 90, 88 are commercially available in any selected length with threads 86 produced by a forming die rather than cutting. Typically the elevating screws are 4140 alloy steel which has been heat treated and stress relieved.

Rolled threads have greater uniformity than cut threads; the greater uniformity reduces the likelihood of jamming of the carriage when the carriage is raised and lowered by rotation of crank handle 72 rotating spindle 54 about elevating screw 38. Preferably the threads are ⅜ inch number 6 Acme.

Bearing collar 70 formed as an integral member and pressfitted into side plate 48 is retained between side plate 48 and bevel gear 66 by running contact of bevel gear 66 with externally facing annular surface 82. This prevents bearing collar 70 from flipping out of side plate 48 and jamming the gear train. Bearing collar 70 protrudes only slightly, if at all, from outwardly facing surface 49A of side plate 48 as illustrated in FIG. 5, permitting the combination of the end of second shaft 68 and cranking handle 72 to be short in distance "A" in FIG. 5. This short dimension reduces bending moment applied to second shaft 68 as an operator turns cranking handle 72. This reduces stress and deformation of the second shaft-bevel gear 68, 66 combination.

Referring to FIG. 8, annular ring 94 about sleeve 92 of spindle 54 prevents spindle 54 from tilting with respect to elevating screw 38 when carriage 44 is moved. Ring 94 retains spindle 54 in alignment with the passageway through spacer block 52 and with the axis of elevating screw 38. Such alignment maintenance contributes to smoother operation when the carriage is raised or lowered and eliminates a potential cause of spindle 54 jamming about elevating screw 38.

The replaceable character of elevating screw 38 is especially important since if workpiece 108 is incorrectly positioned on anvil 106, when carriage 44 is lowered to position ball 110 against workpiece 108, a bending moment will be applied to rearward elevating screw 38. If sufficient force is applied, rearward elevating screw 38 will bend forward, necessitating replacement thereof. Since elevating screw 38 is easily replaceable, user costs are reduced.

An operator raises and lowers carriage 44 along elevating screws 38 by rotating cranking handle 72 with rotational motion applied thereto via gripping of knob 74. Rotation of cranking handle 72 results in unitary rotation of second shaft 68 and driving bevel gear 66. Rotation of driving bevel gear 66 rotates driven bevel gear 64 and shaft 58 on which driven bevel gear 64 is mounted. The complemental engagement of the teeth of bevel gears 66, 64 assures rotation of bevel gear 64 upon rotation of bevel gear 66. Rotation of first shaft 58 produces unitary rotation of idler gear 56. Due to driving engagement of idler gear 56 with external teeth of spindle 54, rotation of first shaft 58 and idler gear 56 produces rotation of spindle 54. As spindle 54 rotates, engagement of internal teeth of spindle 54 with threads 86 of elevating screw 38 moves spindle 54 axially along elevating screw 38. Spindle 54, being connected to carriage 44 via spacer block 52, carries carriage 44 as spindle 54 moves axially along elevating screw 38.

We claim:

1. Apparatus for supporting a Brinell method metal hardness test head comprising:
   (a) a base including:
      (i) a central portion of generally rectangular parallelepiped configuration;
      (ii) a plurality of coplanar petal-like supports integral with and extending outwardly from a lower part of said central portion;
   downwardly facing surfaces of said central portion and said supports being coplanar and contiguous with one another;
      (iii) an anvil support portion integral with and extending laterally in cantilever fashion from said central portion remote from said downwardly facing surface of said central portion, having an upwardly facing planar anvil support surface;
      (iv) webs perpendicular to said contiguous downwardly facing surface, integral with said central portion and said supports, providing bracing between upper surfaces of said supports and lateral surfaces of said central portion;
   said central portion including a threaded bore perpendicular to and opening oppositely from said downwardly facing contiguous surface;
   said central portion including an external lateral bore perpendicular to and intersecting said threaded bore;
   (b) an elevating screw in threaded engagement with said threaded bore and including a lateral bore therein communicating with said lateral bore of said central portion;
   (c) means within said communicating lateral bores for bracing said elevating screw against movement relative to said bore;
   (d) a carriage for supporting said test head above said anvil support portion, movable along said elevating screw, including:
      (i) a pair of spaced-apart parallel side plates bracketing said elevating screw therebetween;
      (ii) a spacer block between and connected to said side plates, said elevating screw passing through a passageway therewithin;

(iii) an internally and externally toothed spindle journaled in said spacer block passageway for rotation about an axis parallel therewith, internal teeth of said spindle drivingly engaging said threaded elevating screw;

(iv) an idler gear journaled between said parallel plates and drivingly engaging said external teeth of said spindle;

(v) a driven bevel gear mounted on a common first shaft and rotatable unitarily with said idler gear;

(vi) a driving bevel gear, mounted on and rotatable unitarily with a second shaft, in driving engagement with said driven bevel gear;

(vii) said second shaft extending through a first one of said side plates;

(viii) a cranking handle connected to said second shaft outboard of said first side plates, facilitating rotation of said second shaft by an operator turning said handle;

(ix) a bearing collar separating said driving bevel gear and said second shaft from said first side plate, immovable with respect to said side plates and including:

(1) a shoulder portion having axial length at least equal to thickness of said first side plate and an axial bore therein journaling a portion of said driving bevel gear for rotation of said second shaft relative to said collar; and (2) a flange portion, abutting an inwardly facing surface of said first side plate, extending radially outwardly about said shoulder portion at least to where driving bevel gear periphery is at least oblique to said inwardly facing surface of said first plate.

2. Apparatus of claim 1 wherein a lower surface of said anvil support portion tapers upwardly relative to said central portion downwardly facing surface and lateral surfaces of said anvil support portion taper inwardly relative to lateral surfaces of said central portion to define an anvil support portion of substantially reduced width and height, at the portion thereof which is remote from said central portion, relative to said central portion.

3. Apparatus of claim 2 wherein said anvil support surface is parallel to said downwardly facing surface of said central portion.

4. Apparatus of claim 3 wherein said central portion, said anvil support portion, said petal-like supports and said webs are integrally formed as a unitary piece of cast aluminum.

5. Apparatus according to claim 4 wherein said elevating screw bracing means is a hollow longitudinally slotted cylindrical member.

6. Apparatus according to claim 5 wherein said cylindrical member is highly elastic spring steel.

7. Apparatus according to claim 1 wherein threads of said elevating screw and internal teeth of said spindle have complementally curved crests and roots.

8. Apparatus according to claim 1 wherein said shoulder and flange portions of said bearing collar are integrally formed from a unitary piece of brass.

9. Apparatus according to claim 8 wherein said shoulder of said bearing collar has axial length in excess of thickness of said first side plate; wherein said flange portion of said bearing collar abuts said inwardly facing surface of said first side plate and wherein said shoulder portion of said bearing collar presents an outwardly facing surface axially remote from said collar portion, in running contact with said cranking handle during rotation of said second shaft, thereby separating said cranking handle from said first side plate.

10. Apparatus according to claim 1 wherein said threaded bore in said central portion extends entirely through said central portion and has an opening in said downwardly facing surface of said central portion; wherein said elevating screw is in threaded engagement with said threaded bore over the entire length of said bore.

11. Apparatus of claim 1 further comprising:
(a) an annular sleeve portion of said spindle protruding outwardly from within said spacer block, slideably receiving said elevating screw therewithin;
(b) an annular ring co-axial with and secured about said sleeve external of said spacer block;
said ring interfering with said block upon movement of said spindle along said elevating screw towards said ring.

12. Apparatus of claim 11 wherein said ring has a radial cut therethrough and includes setscrew means bridging said cut for urging said ring closed at said cut upon rotation of said setscrew, a shaft portion of said setscrew threadably engaging a tapped hole in said ring on one side of said cut, said setscrew axis oriented generally tangentially to said ring.

13. Apparatus for supporting a Brinell method metal hardness test head comprising:
a. a base including:
(i) a central portion of generally rectangular parallelepiped configuration;
(ii) a plurality of co-planar petal-like supports integral with and extending outwardly from a lower part of said central portion;
downwardly facing surfaces of said central portion and said supports being co-planar and contiguous with one another;
(iii) an anvil support portion integral with and extending laterally in cantilever fashion from said central portion remote from said downwardly facing surface of said central portion, having an upwardly facing planar anvil support surface, said anvil support surface being parallel to said downwardly facing surface of said central portion, a lower surface of said anvil support portion tapering upwardly relative to said central portion downwardly facing surface and lateral surfaces of said anvil support portion tapering inwardly relative to lateral surfaces of said central portion to define an anvil support portion of substantially reduced width and height, at the portion thereof which is remote from said central portion, relative to said central portion;
(iv) vertically elongated webs perpendicular to said contiguous downwardly facing surface, integral with said central portion and said supports, providing bracing between upper surfaces of said supports and lateral surfaces of said central portion;
said central portion including a threaded bore perpendicular to said downwardly facing contiguous surface and extending entirely through said central portion;
said central portion including an external lateral bore perpendicular to and intersecting said threaded bore;
wherein said central portion, said petal-like supports, said anvil support portion and said webs are formed integrally one with another as a unitary aluminum casting;

b. an elevating screw in threaded engagement with said threaded bore over the entire length of said bore and including a lateral bore therein communicating with said lateral bore of said base central portion;

c. a hollow longitudinally slotted cylindrical member made of highly elastic spring steel, residing within at least part of both of said communicating lateral bores, for bracing said elevating screw against movement relative to said central portion lateral bore;

(d) a carriage for supporting said test head above said anvil portion, movable along said elevating screw including:
  (i) a pair of spaced-apart parallel side plates bracketing said elevating screw therebetween;
  (ii) a spacer block between and connected to said side plates, said elevating screw passing through a passageway therewithin;
  (iii) an internally and externally toothed spindle journaled in said spacer block passageway for rotation about an axis parallel therewith, internal teeth of said spindle drivingly engaging said threaded elevating screw and including an annular sleeve portion protruding outwardly from within said spacer block, slideably receiving said elevating screw therewithin;
  wherein said threads of said elevating screw and said internal teeth of said spindle have complementally curved crests and roots;
  (iv) an idler gear journaled between said parallel plates and drivingly engaging said external teeth of said spindle;
  (v) a driven bevel gear mounted on a common first shaft and rotatable unitarily with said idler gear;
  (vi) a driving bevel gear, mounted on and rotatable unitarily with a second shaft, in driving engagement with said driven bevel gear;
  (vii) said second shaft extending through a first one of said side plates;
  (viii) a cranking handle fixedly connected to said second shaft outboard of said first side plate, facilitating rotation of said second shaft by an operator turning said handle;
  (ix) a bearing collar separating said driving bevel gear and said second shaft from said first side plate, fixedly secured within an aperture in said first side plate and including:
    (1) a shoulder portion having axial length in excess of thickness of said first side plate and an axial bore thereof journaling a portion of said driving bevel gear for rotation of said driving bevel gear and said second shaft therewithin relative to said collar; and
    (2) a flange portion, abutting an inwardly facing surface of said first side plate, extending radially outwardly about said shoulder portion at least to where said driving bevel gear periphery is at least oblique to said inwardly facing surface of said first plate;
    said shoulder presenting an outwardly facing surface axially remote from said flange portion, in running contact with said cranking handle during rotation of said second shaft thereby separating said cranking handle from said first side plate;
  (x) an annular ring co-axial with and secured about said sleeve external of said spacer block, said ring having a radial cut therethrough and including setscrew means bridging said cut for urging said ring closed at said cut upon rotation of said setscrew, a shaft portion of said setscrew threadedly engaging a tapped hole in said ring on one side of said cut, said setscrew axis oriented generally tangentially to said ring;
  said ring interfering with said block upon movement of said spindle along said elevating screw towards said ring.

* * * * *